United States Patent [19]
Sagi et al.

[11] 3,946,612
[45] Mar. 30, 1976

[54] TEMPERATURE INDICATING COMPOSITIONS

[75] Inventors: Zsigmond Sagi, Parsippany, N.J.; Berel Weinstein, New York, N.Y.

[73] Assignee: Bio-Medical Sciences, Inc., Fairfield, N.J.

[22] Filed: Sept. 17, 1973

[21] Appl. No.: 398,011

Related U.S. Application Data

[63] Continuation of Ser. No. 120,998, March 4, 1971, abandoned, which is a continuation-in-part of Ser. No. 58,001, July 24, 1970, Pat. No. 3,665,770.

[52] U.S. Cl. ............................ 73/356; 73/358
[51] Int. Cl. ............................ G01k 11/08
[58] Field of Search .......... 73/356, 358; 116/114.5, 116/114 V; 252/408

[56] References Cited
UNITED STATES PATENTS

| | | | |
|---|---|---|---|
| 2,932,971 | 4/1960 | Moore | 73/356 |
| 3,175,401 | 3/1965 | Geldmacher | 73/358 |
| 3,430,491 | 3/1969 | Gignilliat | 73/358 |
| 3,465,590 | 9/1969 | Kluth | 73/358 |
| 3,597,976 | 8/1971 | Fryar | 73/358 |

*Primary Examiner*—Richard C. Queisser
*Assistant Examiner*—Denis E. Corr
*Attorney, Agent, or Firm*—Anthony Lagani, Jr.

[57] ABSTRACT

Temperature indicating compositions are provided for use in disposable thermometers comprising a heat-conductive carrier sheet having at least one but preferably a plurality of regions (cavities) thereon, each region containing a thermally responsive substance which undergoes a change in state at a precise and predetermined temperature different from any other region. The thermally responsive materials used herein as temperature indicating compositions are solid solutions comprised of two components which, inter alia, have linear temperature-composition liquidous curves. The change of state of the solid solution in each region is readily detectable visually by an indicator system which is intimately associated with the solid solution in said regions in order to permit rapid and accurate visual determination of the temperature of the test subject.

12 Claims, 4 Drawing Figures

TEMPERATURE INDICATING COMPOSITIONS

This is a continuation of Ser. No. 120,998 filed Mar. 4, 1971, now abandoned, which in turn is a continuation-in-part of Ser. No. 58,001 filed July 24, 1970, now U.S. Pat. No. 3,665,770.

BACKGROUND OF INVENTION

Prior Art

For years the conventional mercury thermometer has been the sole temperature indicating device which has been widely used in clinical applications for the measurement of temperature of the human body and for other temperature determinations. However, this type of thermometer has numerous disadvantages which are both inherent in its construction and obvious from its use, and nearly everyone who has had occasion to use such a thermometer is well acquainted with these disadvantages. For example, at least 3 minutes are usually required to obtain a meaningful temperature reading, and once used, it must be sterilized before its next clinical application. The breakable nature of this type of thermometer, the poisonous nature of mercury, the high cost per unit and the care required in packaging, shipping and storage of these thermometers are only a few of their disadvantages.

Various other types of thermometers have heretofore been proposed as substitutes for the conventional mercury thermometer. For example, U.S. Pat. No. 3,465,590 issued Sept. 9, 1969 (L. A. Kluth et al.) describes a thermometer which is disposable after a single application and does not employ mercury as the thermally responsive substance. Rather, Kluth et al. employ mixtures of certain of the even series of saturated fatty acids, e.g., myristic acid, palmitic acid and lauric acid for indication of temperature of the human body within ½° Fahrenheit. Although the use of such thermometers obviates some of the deficiencies of the conventional mercury thermometers, their application is limited to temperature measurements in the range of 96° to 101°F. and its accuracy is restricted to ½° Fahrenheit, thus precluding them from use for more precise temperature measurements and, as a practical matter, they do not provide accurate clinical information regarding the temperature of the human body during a period of fever when the temperature is frequently above 101° Fahrenheit, and is sometimes as high as 103° or even 105° Fahrenheit. Another difficulty with this thermometer is that accurate temperature determination depends upon complete change of state of the solid solution employed as the thermally responsive material. A complete change of state, i.e., from opaque solid to translucent liquid is necessary for a meaningful temperature reading in the thermometer described in the aforementioned patent.

Another type of temperature indicating device is disclosed in U.S. Pat. No. 3,175,401 issued Mar. 30, 1965 (D. E. Geldmacher). This thermometer is provided with several cavities each containing a different thermally indicating composition melting at a different temperature range. Each of the thermally indicating compositions employed by Geldmacher is normally opaque below a certain temperature and become transparent above a certain temperature. Once again, however, as in the Kluth et al. patent, temperature indication is obtained by complete change of state of the thermally responsive material in each cavity. Furthermore, as many as 40 to 50 different chemical compounds will be necessary to cover the desired clinical temperature range. While this patent discloses the use of a mixture of dichlorobenzene and diphenyl, it is noted that dichlorobenzene is merely added to lower the melting temperature of diphenyl. See column 1, lines 15–22 and FIG. 9. Additionally, as will hereinafter be explained, these two compounds, i.e., dichlorobenzene and diphenyl do not form a solid solution of the type encompassed within the scope of this invention.

Still another type of thermometer is described by P. Finkelstein in U.S. Pat. No. 3,521,489 issued July 21, 1970. The temperature indication in this type of thermometer is based upon the flow of a melted material from so-called "holding compartment" into a so-called "flow-inducing receiving element" such as an absorbent material, by a capillary action. See column 1, lines 61–72. As in the Geldmacher patent, however, temperature indication is realized by the use of numerous different thermally responsive chemical compounds, each undergoing a complete change of state at a different predetermined temperature.

There are other types of thermometers which have been suggested as replacements for the conventional mercury thermometer. For example, electronic thermometers have been proposed for this purpose. The temperature detecting elements in this type of thermometers consist of wire probes covered by disposable sheaths. However, such electronic thermometers are generally bulky and cost in the order of several hundred dollars per unit. Also, they require periodic recharging, calibration, servicing and frequent sterilization.

Thus, despite all efforts to provide a more suitable thermometer, the conventional mercury thermometer continues to dominate this field and is still the most prevalent and widely used temperature indicating device in the home and in the various institutions such as hospitals and medical and industrial laboratories

SUMMARY OF INVENTION

The present invention contemplates providing temperature indicating compositions for use in disposable thermometers for measuring the temperature of the human body and for other temperature measurements as well.

In one aspect, this invention contemplates providing thermally indicating compositions which undergo change of state, i.e., from solid to liquid, at precise and predetermined temperature, such temperature indicating compositions being solid solutions of certain organic compounds to be hereinafter described.

In another aspect, the present invention is concerned with providing solid solutions which undergo change of state rapidly over a very narrow temperature range such that temperature indication may be achieved within an accuracy of 2/10th of a Fahrenheit degree and which can be employed for measurement of temperatures within the clinical range, i.e., 96° to 105° F., or wider.

Another aspect of this invention is directed to the use of an indicating system associated with the thermally responsive material so as to obtain a rapid visual indication of the change of state of such material, and hence the temperature of the test subject.

In yet another aspect, the present invention is directed to the addition of certain organic compounds, as hereinafter described, in order to lower the temperature of the incipient fusion of the thermally responsive materials which ordinarily melt at temperatures above the clinical range.

These and other aspects of this invention will be more fully comprehended from the following detailed description taken in connection with the accompanying drawings. Throughout this description, the terms "thermally responsive substance", "thermally responsive material", "temperature indicating compositions" and "solid solutions" are used interchangeably to denote the same material.

DETAILED DISCLOSURE OF THE INVENTION

Description of the Drawings

The details of construction and the relative arrangements of the various elements of a thermometer of the type useful in the present invention are fully set forth in U.S. Pat. No. 3,665,770.

In the drawings appended hereto, where like numerals are used to designate like parts:

Referring now to the drawings, particularly to FIGS. 1 and 2, FIG. 1 shows a thermometer 1 having a handle portion 3 and an indicator portion 5 adapted for insertion into the mouth for oral temperature measurements.

The indicator portion 5 contains a plurality of cavities or regions 7 adequately spaced and distributed on the indicator portion as shown in FIG. 1. Each cavity is filled with a temperature indicating composition 9 melting at a precise and predetermined temperature different from the composition in the next adjacent cavity by 2/10th of a Fahrenheit degree. While FIG. 1 illustrates a plurality of regions 7, it must be understood that only one region may be employed in those instances where the temperature indicator is not used for clinical applications but rather, it is employed to apprise one of a single predetermined temperature or thermal state of the test subject.

Figure 2:
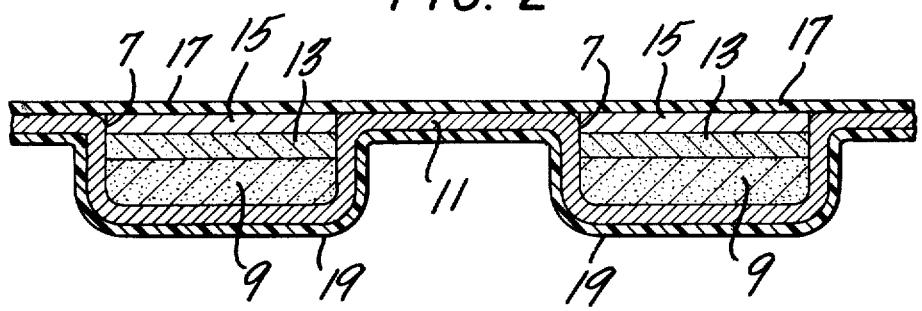
FIG. 2 is a vertical section taken along the line 2—2 of FIG. 1.

As is further shown in FIG. 2, the thermometer 1 is comprised of a carrier sheet 11 which contains the aforesaid cavities 7. Only two such cavities are shown in exaggerated dimensions in order to facilitate understanding of this description.

The carrier sheet 11 is generally provided as a sheet of flexible, heat-conductive material such as an aluminum foil. This will insure rapid heat transfer from the test subject to the temperature indicating compositions in said cavities. While aluminum foil is very convenient for this purpose, flexible, heat-conductive sheets of other materials such as, for example, copper, silver, gold, stainless steel or any other heat-conductive pliable material can be employed with similar efficacy. Naturally the heat-conductive carrier sheet 11 must be made of a material which has a high thermal conductivity, relatively large surface area of contact with the test subject and must be of minimum thickness, while preserving its structural integrity, in order to permit rapid conduction of heat into the thermally responsive substances in said cavities. When aluminum foil is used as the carrier sheet, its thickness may vary from about 0.001 to about 0.004 mil. In any event, the selection of such heat-conductive carrier sheets is well within the knowledge of those skilled in the art and requires no additional elaboration.

Superimposed upon the temperature indicating composition and in intimate contact therewith, there is shown an indicator layer 13 and a masking layer 15 which overlies the indicator layer. The composite indicator layer-masking layer will hereinafter be referred to as the "indicator system" or "indicator means".

A transparent layer 17 such as, for example, polypropylene, polyethylene terephthalates, nitrocellulose, polyvinyl chloride, etc., is provided as a cover film coextensive with and attached to carrier sheet 11 sealably or by any other suitable means. Furthermore, in order to provide structural integrity to the thermometer and to avoid contact between the human mouth and the aluminum foil, the carrier sheet 11 is provided with an undercover layer 19 (usually of similar material as layer 17) which is coextensive with and overlies the lower surface of carrier sheet and conformally contours the aforesaid cavities. This undercover layer is usually adhesively attached to the carrier sheet.

The thickness of the undercover layer is generally in the order of from about 0.001 to about 0.003 mils in order to facilitate rapid heat transfer from the test subject to carrier sheet 11 and hence to the thermally responsive substances in the aforesaid cavities.

If desired, a heat conductive metallic powder may be added to the undercover layer in order to improve its heat transfer characteristics. Powdered metallic aluminum has been found to be particularly satisfactory for this purpose.

Figure 1:
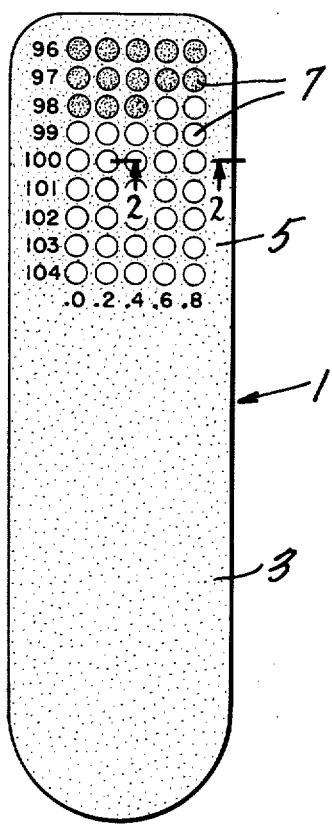
FIG. 1 is a plan view of a thermometer embodying the principles of this invention.

While FIGS. 1 and 2 depict the detailed construction of a thermometer of the type usually employed herein it can be readily appreciated that several structural modifications may be made therein without affecting their usefulness for the purpose of the present invention. For a more detailed description of other embodiments of this type of thermometers, reference may be made to U.S. Pat. No. 3,665,770.

DESCRIPTION OF INVENTION

It has now been unexpectedly discovered that certain organic compounds (to be hereinafter described) form solid solutions which undergo change of state at precise and predetermined temperatures. The term "solid solution" is well known and usually refers to a homogeneous solution of one solid in another.

The solid solutions contemplated in the present invention are comprised of two or more, preferably two different organic compounds with varying percentage compositions. Each solid solution undergoes a rapid change of state at a precise and predetermined temperature.

It has been further discovered that the solid solutions employed herein for clinical applications undergo change of state at precise and predetermined temperatures, the temperature of change of state of the solid solution in each cavity being approximately 2/10th of a Fahrenheit degree different from the temperature of change of state of the solid solution in the adjacent cavity. Thus, for example, in clinical applications where temperature measurements in the range of 96° to 105° Fahrenheit is usually desired, 45 different solid solutions (differing in their percentage compositions but otherwise made from the same two components) will provide all the necessary temperature gradations in increments of 2/10th of a Fahrenheit degree, i.e., 96.0, 96.2, 96.4, etc., up to and including 104.8° Fahrenheit.

It is apparent from the foregoing description that the selection of the organic compounds which respond to the aforesaid requirements requires judicious and careful scrutiny since not all organic compounds are useful for this purpose. Rather, the organic compounds which are particularly adapted for the formations of solid solutions which can serve as temperature indicating compositions in accordance with the present inventions are those having certain common chemical and/or physical properties which serve as criteria for their selection.

Thus it has been discovered that compounds, particularly organic compounds, which have analogous chemical structures (e.g., analogs, homologs and optical isomers), have substantially the same molecular volume or have similar crystalline structure (e.g., isomorphous) and which form solid solutions useful for the purpose of this invention. In addition, the solid solutions must have a linear or an essentially linear temperature-composition liquidous curve, particularly over the desired temperature range such as, for example, over the clinical temperature range.

Exemplary solid solutions of organic compounds, the components of which respond to one or more of the aforesaid criteria are as follows:
 A. Ortho-chloronitrobenzene: Ortho-bromonitrobenzene
 B. 1-menthol: dl-menthol
 C. Acetophenone: Benzophenone
 D. Dimethyl succinate: Dimethyl oxalate
 E. 4-Chloropropiophenone: 4-Bromopropiophenone
 F. 4-Chloro-2-methyl aniline: 4-Bromo-2-methyl aniline
 G. 4-Chloroacetophenone: 4-Bromoacetophenone
 H. n-Butyl sulfoxide: n-Butyl sulfone
 I. n-Hexane: 2-Nonodecane
 J. Cyclohexane: 2-Nonodecane
 K. alpha-Chlorocinnamaldehyde: alpha-Bromocinnamaldehyde.

Among the aforesaid solid solutions, the systems described in A, B, E, F, H and K have been found to be particularly useful in clinical thermometers for temperature measurements within 2/10th of a Fahrenheit degree, or even less. However, the solid solutions made from ortho-chloronitrobenzene and ortho-bromonitrobenzene have been found to be most preferable for use in temperature measurements in the clinical range within the aforesaid accuracy.

Thus, it can be readily observed that whereas the inventions disclosed in U.S. Pat. No. 3,175,401 and U.S. Pat. No. 3,521,489, supra, require numerous different chemicals in order to obtain the desired temperature measurements, the present invention employs solid solutions made of two organic compounds varying only in their percentage compositions. In clinical applications, for example, where temperatures are measured in the range of 96° to 105° F., 45 different thermally responsive compositions are required if temperature is to be measured within 2/10th of a Fahrenheit degree. Unlike the temperature indicating systems described in these two patents, which would require 45 different compounds to cover such temperature gradations, the present invention affords greater simplicity in that only two components are necessary in the form of solid solutions, varying only in the percentage compositions of these components. Since these compounds must be employed in high state of purity, it can readily be appreciated that the use of solid solutions of this invention obviates the necessity for purification of such numerous compounds.

Furthermore, unlike the mixtures described by Kluth et al., supra, the solid solutions employed in the present invention cover a wider temperature range and are capable of more accurate temperature measurements, i.e., within 2/10th rather than 5/10th of Fahrenheit degree which is the limit of accuracy of the Kluth et al. compositions.

Figure 3:
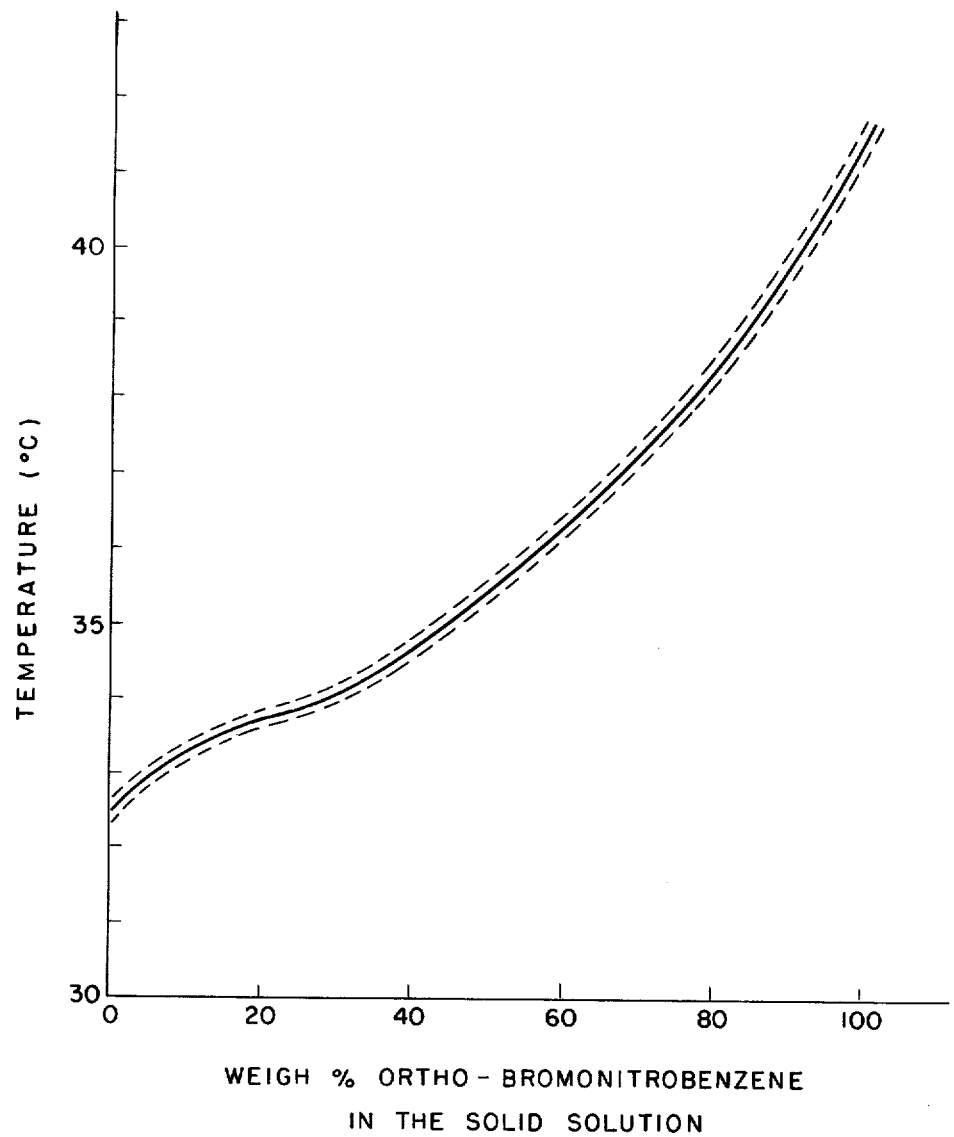
FIG. 3 depicts the liquidous curve of a solid solution of ortho-chloronitrobenzene and ortho-bromonitrobenzene. The band defined by the dashed lines in this diagram represents the limit of accuracy of temperature measurements, i.e., 2/10th of Fahrenheit degree. The band is shown in exaggerated width in order to facilitate this illustration.

In order to facilitate the understanding of the solid solution systems employed as temperature indicating compositions in the present invention and their advantages over the systems described by Kluth et al., reference may be had to FIG. 3 of this application and compared to a similar diagram shown as FIG. 10 in the Kluth et al. patent, supra. It is at once apparent from this comparison that the solid solutions of this invention undergo a change of state more rapidly and over a narrower temperature range than the mixtures described by Kluth et al.

The preparation of solid solutions in general is well known to those skilled in the art and requires no detailed description herein. Nevertheless, the ensuing description is intended to provide a basis for the preparation of solid solutions which are particularly useful in the present invention.

As was previously mentioned, FIG. 3 depicts a temperature-composition curve (liquidous curve) for solid solutions of ortho-bromonitrobenzene and ortho-chloronitrobenzene. As it is observed from this Figure, the liquidous curve is essentially linear.

In preparing a solid solution of ortho-chloronitrobenzene and ortho-bromonitrobenzene, one simply mixes predetermined amounts of these components calculated to give a solid solution having the desired melting point. Thus in order to prepare a solid solution having a melting point of, for example, 101.4° Fahrenheit, one would mix the appropriate amounts of the two components as selected from the curve shown in FIG. 3, calculated to give the desired melting point. Solid solutions having other melting points may be prepared in a similar manner using varying amounts of the two components and, in each instance, the precise melting point of the solid solutions are determined before they are charged into the cavities of the thermometer. Solid solutions composed of other components may be similarly prepared.

For the purpose of illustration, the relative compositions of solid solutions of ortho-chloronitrobenzene and ortho-bromonitrobenzene and the corresponding melting points of these solid solutions are given in the following table:

TABLE

| TEMPERATURE, °F | COMPOSITION IN WEIGHT PERCENT | |
|---|---|---|
| | ORTHOBROMO-NITROBENZENE | ORTHOCHLORO-NITROBENZENE |
| 96.0 | 56.2 | 43.8 |
| 96.2 | 57.5 | 42.5 |
| 96.4 | 58.8 | 41.2 |
| 96.6 | 60.1 | 39.9 |
| 96.8 | 61.3 | 38.7 |
| 97.0 | 62.5 | 37.5 |
| 97.2 | 63.5 | 36.5 |
| 97.4 | 64.5 | 35.5 |
| 97.6 | 65.5 | 34.5 |
| 97.8 | 66.5 | 33.5 |
| 98.0 | 67.5 | 32.5 |
| 98.2 | 68.5 | 31.5 |
| 98.4 | 69.5 | 30.5 |
| 98.6 | 70.5 | 29.5 |
| 98.8 | 71.5 | 28.5 |
| 99.0 | 72.5 | 27.5 |
| 99.2 | 73.5 | 26.5 |
| 99.4 | 74.5 | 25.5 |
| 99.6 | 75.5 | 24.5 |
| 99.8 | 76.4 | 23.6 |
| 100.0 | 77.3 | 22.7 |
| 100.2 | 78.1 | 21.9 |
| 100.4 | 79.0 | 21.0 |
| 100.6 | 79.9 | 20.1 |
| 100.8 | 80.8 | 19.2 |
| 101.0 | 81.7 | 18.3 |
| 101.2 | 82.6 | 17.4 |
| 101.4 | 83.5 | 16.5 |
| 101.6 | 84.3 | 15.7 |
| 101.8 | 85.1 | 14.9 |
| 102.0 | 85.9 | 14.1 |
| 102.2 | 86.7 | 13.3 |
| 102.4 | 87.5 | 12.5 |
| 102.6 | 88.2 | 11.8 |
| 102.8 | 88.9 | 11.1 |
| 103.0 | 89.6 | 10.4 |
| 103.2 | 90.3 | 9.7 |
| 103.4 | 91.0 | 9.0 |
| 103.6 | 91.7 | 8.3 |
| 103.8 | 92.4 | 7.6 |
| 104.0 | 93.1 | 6.9 |
| 104.2 | 93.8 | 6.2 |
| 104.4 | 94.5 | 5.5 |
| 104.6 | 95.2 | 4.8 |
| 104.8 | 96.0 | 4.0 |

While generally the amount of solid solution in each cavity need only be sufficient to wet the indicator or cause a change in its color, as a practical matter and in order to obtain more reliable temperature measurements with good consistency, sufficient amount of the solid solution must be employed in each cavity so that at least about 70% of the indicator area associated with said region has been wetted or changed in color. It can be appreciated, therefore, that in addition to the amount of the temperature indicating composition in each cavity, the size of the cavity, the porosity of the indicator and its thickness are some of major factors which must be considered and judiciously selected for rapid visual detection and accurate measurement of the temperature in each region. Nevertheless, it must be emphasized that these variables may be ascertained by those skilled in the art within the guidelines provided in this description without departing from the spirit of this invention.

The cavities may be filled with the solid solutions by known means such as, for example, by metering predetermined quantities therein, or by another suitable means adapted for mass production.

As was previously stated, the change of state of the solid solutions in each cavity can be visually detected by an indicator system which is in intimate contact with the solid solutions in each of the cavities. As was previously mentioned, the indicator system is a composite of an indicator layer and a masking layer. The indicator layer is usually a highly absorbent paper which has a high porosity and a high wick action in order to facilitate its wetting upon change of state of the thermally responsive materials in said cavities. This layer may be impregnated with a dye or a pigment to provide a color indication of such change of state.

The masking layer is ordinarily a paper having the same general properties as the indicator layer but which is of contrasting color. Thus, upon change of state of the thermally responsive substance in each cavity, the liquid is rapidly absorbed by the indicator layer and dissolves the dye or pigment therein. The resulting dye or pigment solution (or dispersion) migrates through the indicator layer into the masking layer thereby facilitating visual detection of the change in color of the masking layer. Accordingly, temperature measurements may be made irreversibly and the thermometer may be disposed of after a single use. However, in non-clinical applications, the thermometer may be employed for measuring temperatures higher than the previously registered temperature.

The dye or pigment employed may be incorporated into the indicator 13 or it may be added to the solid solution directly. When incorporated in the indicator layer, the latter may be simply dipped into the dye solution or into a dispersion of the pigment, or it may be sprayed or coated with such a solution or dispersion. Naturally sufficient amount of dye or pigment must be incorporated so as to facilitate rapid visual detection of the color change in each cavity.

If added directly to the solid solution, once again the amount of dye or pigment employed must be sufficient to permit rapid visual detection of the color change as aforesaid. However, the addition of a dye or a pigment directly to the solid solutions may, in some instances, adversely affect their melting ranges. Thus, in those instances where very accurate temperature measurements are required, i.e., within 2/10th of a Fahrenheit degree, the former method is preferable unless the dye or pigment selected for this purpose is known to have no adverse effects upon the accuracy of the melting point ranges of the solid solutions.

Whether the dye or pigment is added directly to the solid solution or incorporated into the indicator, it is advisable to prevent contact between the solid solution in said cavities and the indicator until the thermometer is actually in use. This prevents possible contamination of the solid solutions with the dye or the pigment. Thus, a separator layer (not shown) may be provided to prevent such contact and possible contamination. This separator may be pealably removed when the thermometer is ready for use. The details of construction of such a separator are described in the aforesaid U.S. Pat. No. 3,665,770.

While the indicator means or systems has heretofore been described with certain degrees of particularity in order to facilitate the understanding of this invention, it must be emphasized that this description is provided herein solely for the purpose of such understanding and is not intended to limit the scope of the present invention. Other indicator systems may be employed for the purpose of detecting the temperatures corresponding to changes of state of solid solutions. For a detailed description of such indicator systems see the aforesaid U.S. Pat. No. 3,665,770.

Generally, oil-soluble dyes which are compatible with the liquid resulting from change of state of the solid solutions in the aforesaid cavities have been found to be particularly suitable for incorporation into the indicator for use in the present invention.

In the case of pigments, it has been discovered that improved liquid absorption and color indication may be achieved by using pigments having particle sizes ranging from about 0.2 to about 0.5 microns, rather than using pigments with substantially larger particle sizes, e.g., one micron or greater. It must be pointed out, however, that the advantages of the present invention may be realized using any dye or pigment which will facilitate visual detection of the change of state of the solid solution in each cavity.

It must be further pointed out that unlike the temperature indicating compositions which have heretofore been employed in the prior art as exemplified by the aforesaid patents, even before complete change of state of the solid solutions employed herein, the liquid is instantaneously absorbed by and spread through the indicator system so as to apprise one of the precise temperature at which such change of state has occurred. It is therefore at once apparent that complete change of state is not necessary for such temperature measurements.

Figure 4:
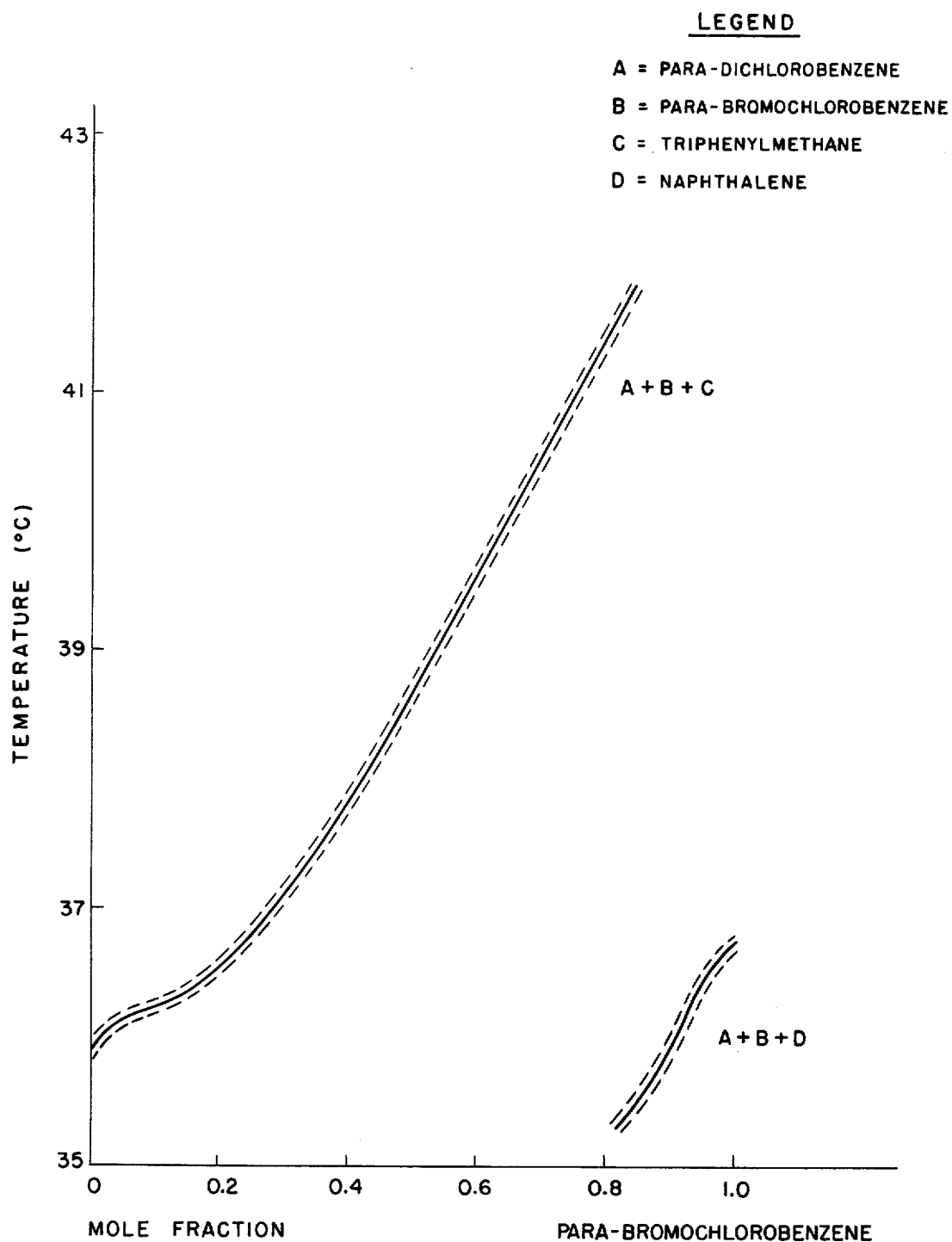
FIG. 4 shows the liquidous curves for solid solutions of para-dichlorobenzene and para-bromochlorobenzene to which naphthalene (lower curve) or triphenylmethane (upper curve) has been added, respectively. Again, as in FIG. 3, the band defined by the dashed lines (shown in exaggerated width) represents the limit of accuracy temperature determinations using these curves. The details of FIG. 4 will be discussed, infra.

While the present invention has heretofore been described with specific reference to solid solutions having melting points within the clinical range, i.e., 96.0° to 104.8° F., it must be understood that this invention is not limited to the use of such compositions. Other solid solutions having melting points above 104.8° F. may be successfully employed by the addition of certain third components which are capable of reducing the melting points of these solid solutions without affecting the linear relationship between the melting points on the one hand, and compositions of the constituents of the solid solutions, on the other hand. Thus, for example, it has been found that para-dichlorobenzene (m.p. 53° C. or 127.6° F.) and para-bromochlorobenzene (m.p. 67.4° C. or 153.1° F.) can be used to prepare solid solutions having melting points within the clinical temperature range. This can be achieved by the addition of specified amounts of naphthalene or triphenylmethane to mixtures of para-dichlorobenzene and para-bromochlorobenzene. Thus, with specific reference to FIG. 4, the upper curve represents compositions in which the relative amounts of para-dichlorobenzene and para-bromochlorobenzene are readily determinable from the abscissa. The amount of triphenylmethane in the mixture is between about 44 and 45 weight percent and is preferably about 45 weight percent of the entire mixture, i.e., para-dichlorobenzene, para-bromochlorobenzene and triphenylmethane. Similarly, the amount of naphthalene in the lower curve is between about 33 and 34 weight percent and is preferably about 33.5 weight percent of the total mixture, i.e., para-dichlorobenzene, para-bromochlorobenzene and naphthalene.

It is readily observed that the addition of such third components lowers the melting point of the solid solution to the desired temperature range. Naturally, the third component and the amount required differ for solid solutions of other components.

While the use of the aforementioned temperature indicating compositions has been illustrated in conjunction with thermometers for the purpose of temperature measurements, it must be pointed out that such illustration is not intended to be either exclusive or limiting. Thus, these temperature indicating compositions can be equally useful in other applications such as, e.g., pyrometers, and to detect overheating of transformers, motors and other similar electrical or mechanical appliances. Naturally for such applications, the temperature (or thermal) indicator system must be modified so that it may be adapted for use in such environments. Such modifications, however, are within the skill of the art and do not alter or affect the spirit of this invention. Nevertheless, it must be emphasized that when used for the determination of temperature within the clinical range, the temperature indicating compositions can be employed to detect the temperature of the human body within 2/10th of a Fahrenheit degree or even less.

When used for clinical temperature determination, it is recommended that the thermometer be inserted in the mouth in contact with the tongue for a period of from about 30 to about 60 seconds. The thermometer may then be removed and the temperature determined by observing the last region which has exhibited the aforesaid changes in color (see FIG. 1). While this time interval is generally satisfactory to achieve measurement of temperature within the desired accuracy, i.e., 2/10th of a Fahrenheit degree (or less), a period of about 30 seconds has generally been found to be adequate in most instances.

It must further be pointed out that while the aforesaid solid solutions have heretofore been described in connection with clinical thermometers for oral temperature measurement of the human body, such thermometers may also be employed for other temperature measurements. However, when used for other applications, the temperature scale will be slightly shifted, without, however, affecting the accuracy of the temperature readings. This is due to the difference in the prevailing environmental conditions which affects the rate of heat transfer from the test subject to the solid solutions. Thus, for example, when the clinical thermometer is used to measure the temperature of a liquid bath, the temperature scale will be shifted by 4/10th of a Fahrenheit degree for the entire clinical range. Thus, the region which would indicate a temperature of 99.4° F. when used for oral temperature measurement, will now measure a liquid bath temperature which is 99.0° F. Such calibrations and adjustments in temperature scale, however, may be made in advance for other such applications, without affecting the accuracy of the temperature measurements.

The invention that is claimed is:

1. A temperature indicating device comprising a heat conducting carrier having a plurality of spaced regions defined therein, a like plurality of solid solutions of at least two organic compounds in varied composition ratios deposited in said regions, a single composition of said solid solutions being deposited in a single one of said regions, said solid solutions having an essentially linear melting point-to-composition relationship over the composition ratio range represented by said plurality of solid solutions, and indicator means associated with said deposited solid solutions and operable to indicate the melting of any individual solid solution.

2. A temperature indicating device according to claim 1 wherein said indicator means comprise a dye or pigment soluble in said solid solutions.

3. A temperature indicating device according to claim 1 wherein said solid solutions are binary mixtures of the same two organic compounds.

4. A temperature indicating device according to claim 3 wherein said binary mixture is selected from the group consisting of o-chloronitrobenzene:o-bromonitrobenzene; l-menthol:dl-menthol; dimethyl succinate:dimethyl oxalate; 4-chloro-2-methylaniline:4-bromo-2-methylaniline; and n-butylsulfoxide:n-butylsulfone.

5. A temperature indicating device according to claim 4 wherein said binary mixtures are composed of o-chloronitrobenzene and o-bromonitrobenzene.

6. A temperature indicating device according to claim 5 wherein said binary mixtures of o-chloronitrobenzene and o-bromonitrobenzene having weight percent composition ratios of from 43.8:56.2 to 4.0:96.0, respectively.

7. A temperature indicating device according to claim 1 wherein said solid solutions are ternary mixtures of the same three organic compounds.

8. A temperature indicating device according to claim 7 wherein the amount of one of said three organic compounds is fixed in all of said solid solutions and the remaining two are varied.

9. A temperature indicating device according to claim 8 wherein said ternary mixtures consist of varied amounts of p-dichlorobenzene and p-bromochlorobenzene and a fixed amount of triphenylmethane.

10. A temperature indicating device according to claim 8 wherein said ternary mixtures consist of varied amounts of p-dichlorobenzene and p-bromochlorobenzene and a fixed amount of naphthalene.

11. A thermometer comprising a heat conducting carrier having a plurality of spaced cavities defined therein, a like plurality of solid solutions of ortho-chloronitrobenzene and ortho-bromonitrobenzene in different weight percent composition ratios deposited in said cavities, a single composition being deposited in a single region, an absorbent indicator layer overlying and in intimate contact with each of said deposited solution and impregnated with a dye or pigment soluble in said solution when said solutions are in the liquid phase and an absorbent masking layer overlying and in intimate contact with said indicator layer, said masking layer being of a color contrasting with that of said dye or pigment but operable to assume the color of the dye or pigment through absorption of melted solution carrying said dye or pigment.

12. A thermometer according to claim 11 including a transparent layer coextensive with said carrier and carrying said indicator and masking layers, said cover layer being operable to position and maintain each of said indicator layers in contact with the deposited solid solution with which it is associated.

* * * * *